United States Patent
Mei

(10) Patent No.: US 9,586,894 B2
(45) Date of Patent: Mar. 7, 2017

(54) PREPARATION METHOD OF SOLID ACRYLAMIDEALKYL SULFONATE

(71) Applicant: Longyi Mei, Nanjing, Jiangsu Province (CN)

(72) Inventor: Longyuan Mei, Hefei (CN)

(73) Assignee: Longyi Mei, Nanjing (CN)

( * ) Notice: Subject to any disclaimer, the term of this patent is extended or adjusted under 35 U.S.C. 154(b) by 0 days.

(21) Appl. No.: 14/765,315

(22) PCT Filed: Jan. 24, 2014

(86) PCT No.: PCT/CN2014/071389
§ 371 (c)(1),
(2) Date: Nov. 9, 2015

(87) PCT Pub. No.: WO2014/117685
PCT Pub. Date: Aug. 7, 2014

(65) Prior Publication Data
US 2016/0122295 A1    May 5, 2016

(30) Foreign Application Priority Data
Feb. 4, 2013 (CN) .......................... 2013 1 0044319

(51) Int. Cl.
*C07C 303/32* (2006.01)
*C07C 303/44* (2006.01)

(52) U.S. Cl.
CPC .......... *C07C 303/32* (2013.01); *C07C 303/44* (2013.01)

(58) Field of Classification Search
CPC .... C07C 303/22; C07C 303/44; C07C 303/32
See application file for complete search history.

(56) References Cited

U.S. PATENT DOCUMENTS 6,331,647 B1 * 12/2001 Quinn ................... C07C 303/44
562/105

* cited by examiner

*Primary Examiner* — Shailendra Kumar
(74) *Attorney, Agent, or Firm* — Kilpatrick Townsend & Stockton LLP

(57) ABSTRACT

The present invention provides a method for preparing a solid acrylamide alkyl sulfonate. Said method comprises: reacting 2-acrylamido-2-methylpropanesulfonic acid and analogs thereof with an alkaline substance in a solvent. The 2-acrylamido-2-methylpropanesulfonic acid and the analogs thereof and the alkaline substance are significant excess with respect to the solvent, so that the amount of the resulting acrylamido alkyl sulfonate exceeds the solubility under the reaction condition. The acrylamido alkyl sulfonate can be continuously generated and directly massively precipitated, and the precipitated solid product, i.e. the product, is collected. The method of the present invention can greatly improve production efficiency of products, save time, reduce cost, and easy to operate by leaving out the re-crystallization step and the like in the prior art.

10 Claims, No Drawings

PREPARATION METHOD OF SOLID ACRYLAMIDEALKYL SULFONATE

CROSS-REFERENCE TO RELATED APPLICATIONS

This application is a national phase application under 35 U.S.C. 371 claiming priority to PCT/CN2014/071389, filed Jan. 24, 2014, which application claims priority to CN201310044319.X, filed Feb. 4, 2013, the teachings of which are hereby incorporated by reference in their entireties for all purposes.

TECHNICAL FIELD

The present invention relates to the field of the preparation and separation of a compound, and particularly to a method for preparing as well as separating solid salt of acrylamido alkyl sulfonic acids.

BACKGROUND ART

2-Acrylamido-2-methylpropanesulfonic acid and analogues thereof, mainly as a co-monomer and homo-monomer, are widely used in many industries. This kind of compounds is a strong acidic substance. Before use, it is usually neutralized with an alkaline substance to prepare a salt solution of pH7-10, for example. This neutralization process has certain technical difficulty, since it is necessary to avoid problems, such as, unwanted yellowness of the solution, increased viscosity, and even a large scale of self-polymerization. Therefore, some users (factories) do not purchase acidic solid itself of such compounds, but purchase the aqueous solution of salt generated after neutralization from a manufacturer, the weight percent concentration thereof being usually 50%~58%. This aqueous solution, as a commodity in transaction, has some unfavorable factors, such as higher cost of intercontinental ocean transportation, but only about half of it is the effective substance really needed, and the rest of the transportation is just water. For high concentration of polymeric monomer solution, it is necessary to make as short as possible the storage time in a factory for manufacturing or using it and the transportation time for transporting it between two places, so as to avoid the possible increase in viscosity or even a large scale of polymerization. Moreover, there are some special requirements for transport and storage conditions, such as avoiding direct sunlight, requiring ventilation to avoid too high temperature and so on. In addition, the product of aqueous solution is not suitable for uses in some non-aqueous systems, and the solution, the highest concentration of which is 50~58%, is also not suitable for usages demanding a higher concentration.

In literature and production practice, re-crystallization and purification of 2-acrylamido-2-methylpropanesulfonic acid solid itself are introduced widely, but a final product of these refining processes is acidic solid itself of 2-acrylamido-2-methylpropanesulfonic acid, rather than derivative salts after the neutralization reaction thereof. U.S. Pat. No. 6,331,647B1 describes a method for preparing solid of derivative salt obtained through a neutralization reaction of such compounds for the purpose of purification. The method comprises: making this kind of acidic compounds completely react with a alkaline substance in water at pH of 7 to 12.5 at −20° C.~75° C.; removing any solids by filtration; and performing re-crystallization on the solution, so as to obtain again a solid which is purified but present in a form of a salt. The re-crystallization is achieved by increasing the temperature and/or performing concentration through removing water and reducing pressure, or reducing the solubility of targets by decreasing the temperature. This method requires that the substance to be purified is completely dissolved in water, therefore during the later process for obtaining a solid again by re-crystallization, it is necessary to consume a lot of energy if the concentration through removing water is applied; and the effect is limited and a large amount of targets would also be dissolved in water if the approach of decreasing the temperature is applied. Thus, this method is more difficult to be commercialized in terms of cost and efficiency, and currently this kind of industrialization salts in a solid form has not appeared in the market.

DISCLOSURE OF THE INVENTION

An object of the present invention is to provide a method for preparing solid acrylamido alkyl sulfonate, which has low cost, high efficiency, and easy operation, so as to solve the technical problems in prior art, such as high preparation cost, low efficiency, difficult commercialization and the like.

The present invention provides a method for preparing solid acrylamido alkyl sulfonate, comprising the steps of:

(1) reacting a material A with a material B in a solvent C to form a product D, wherein the material A comprises at least one of compounds represented by the following general formula:

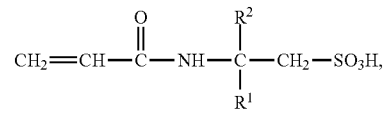

wherein $R^1$ and $R^2$ are hydrogen and/or alkyl groups containing 1 to 20 carbon atoms; the material B is a alkaline substance; and the product D is acrylamido alkyl sulfonate, and wherein the amount of the material A and material B is significantly excess with respect to the solvent C, so that the amount of the product D formed by the reaction between the material A and the material B exceeds the solubility thereof under the reaction condition, and the product D can be continuously generated and directly precipitated (crystallized), thereby leaving out the steps consuming energy and time, such as concentration for removing the solvent or crystallization by reducing the temperature and the like;

(2) collecting the solid product D, namely the product of the method.

In the method for preparing solid acrylamido alkyl sulfonate of the present invention, during adding the materials, the material A and material B are added into the solvent C separately, or the material A and material B in powder state are first sufficiently uniformly mixed according to a preset proportion, and then added into the solvent C to react.

In the method for preparing solid acrylamido alkyl sulfonate of the present invention, the feeding and the discharging in Step (1) can be performed in a batch-wise mode or a continuous mode or in combination of the two modes. The batch-wise feeding mode means that the reaction materials are added into a reaction apparatus in batches. The continuous feeding mode means that the reaction materials are uniformly continuously added into the reaction apparatus during the whole reaction process. The batch-wise discharging mode means that the reaction product is discharged from the reaction apparatus in bathes when being accumulated to a certain amount during the reaction. The continuous discharging mode means that the reaction product is continuously discharged while the reaction is in progress.

In the method for preparing solid acrylamido alkyl sulfonate of the present invention, liquid obtained by the solid-liquid separation is mother liquid, and the solvent C further comprises mother liquid obtained in the previous preparation, and the content thereof is 0 to 100%.

Step (2) has one of the following: direct collecting moisture-containing solid product D containing a certain amount of solvent; direct drying without a solid-liquid separation to remove part of the solvent to obtain a solid product D; direct drying without a solid-liquid separation to remove all the solvent to obtain a solid product D, performing a solid-liquid separation and drying to remove part of the solvent to obtain a solid product D, and performing the solid-liquid separation and drying to remove all the solvent to obtain a solid product D.

In the method for preparing solid acrylamido alkyl sulfonate of the present invention, the amount of the product D resulting from the material A and the material B is greater than its solubility in the solvent C, so that a significant amount of the product D is precipitated, but the material mixture is still not too dry when the reaction is finished, thus solid-liquid separation can be performed by using an ordinary solid-liquid separation method (such as filtration or centrifugation), to obtain a solid and mother liquid.

In the method for preparing solid acrylamido alkyl sulfonate of the present invention, the amount of the product D resulting from the material A and the material B is much greater than its solubility in the solvent C, so that the material mixture is relatively too dry when the reaction is finished, so that no meaningful amount of liquid can be obtained or no liquid can be obtained by using a ordinary solid-liquid separation method (such as filtration and centrifugation), thus no solid-liquid separation step is required in the course of collecting the product, and it goes directly to the drying step instead.

In the method for preparing solid acrylamido alkyl sulfonate of the present invention, the preparation process is performed at a temperature of $-20°$ C.~60° C., preferably at 0~25° C.

The mass ratio of the material A to the solvent C is in the range of 1:1~20:1.

The molar ratio of the material A to material B is in the range calculated in the following manner:

for the material B having monovalent in the acid-base reaction, the molar ratio of the material A to material B is between 1:0.5 to 1:2, preferably 1:1; and for the material B having bivalent in the acid-base reaction, the molar ratio of the material A to material B is between 1:0.25 to 1:1, preferably 1:0.5.

In Step (1), the reaction has a reaction endpoint comprising one of the following conditions being reached:

I. Equilibrium pH of the system is between 5~11, preferably between 8~9.5;

II. the reactants of the designed amounts are exhausted; and

III. the amount of the solvent contained in the product D reaches the preset value.

In the method for preparing solid acrylamido alkyl sulfonate of the present invention, the step (1) can further comprise adding a concentration of 0 mg/kg~1000 mg/kg of a polymerization inhibitor and/or feeding oxygen or air.

In the method for preparing solid acrylamido alkyl sulfonate of the present invention, the material B comprises at least one of the following substances: a metal oxide, a metal hydroxide, and a compound with the structure $NR^3R^4R^5$, wherein $R^3$ and $R^4$ and $R^5$ are hydrogen, or an alkyl group, an alkoxy group, or an alkanol each containing 1 to 10 carbon atoms.

The solvent C comprises at least one of the following solvents: water, alcohol containing 1 to 8 carbon atoms, ketone containing 1 to 8 carbon atoms, ether containing 1 to 8 carbon atoms, ester containing 1 to 8 carbon atoms, and alkane and halogenated alkane containing 1 to 8 carbon atoms.

In the method for preparing solid acrylamido alkyl sulfonate of the present invention, the material B is one of NaOH, KOH, LiOH, $Ca(OH)_2$, $Mg(OH)_2$, $Na_2O$, $K_2O$, $Li_2O$, CaO, MgO, $NH_3$, methylamine, dimethylamine, trimethylamine, ethylamine, diethylamine, triethylamine, propylamine and butylamine or mixture of more thereof.

The method for preparing solid acrylamido alkyl sulfonate of the present invention differs from the prior art at that: in the method of the present invention, an excessive amount of acrylamido alkyl sulfonic acids is made to react with alkaline substance, such that a large amount of deposit of the resulting acrylamido alkyl sulfonate is automatically precipitated out during the reaction without other processing, and the product is obtained either directly after completion of the reaction or after the solid-liquid separation, thereby eliminating the costly and time-consuming steps in prior art, such as the evaporation concentration or the re-crystallization by decreasing the temperature, which is employed in the process of obtaining solid, so as to greatly improve the production efficiency of products, save time, and reduce the cost, and thus industrialized production of such solid salts having economic value is made possible, and the solid salts as new industrialized commodities, emerge on the market. The dry solid product prepared can be suitable for usages in non-aqueous systems, and can also be used in conditions where the solution product of the effective content more than 50%-58% is needed. In the method of the present invention, mother liquid obtained by the solid-liquid separation can be reused, which is environmentally friendly and energy-saving, safe and reliable. The preparation method of the present invention is simple and feasible, and easy to operate.

DETAILED DESCRIPTION

In the method for preparing solid acrylamido alkyl sulfonate of the present invention, the amount of the material A and material B is significantly excess with respect to the solvent C, so that the amount of the product D generated by the reaction exceeds the solubility thereof under the reaction condition, thus the product D can be continuously generated and directly massively precipitated out, and the product D can be directly used as: a moisture-containing solid product D containing a certain amount of the solvent without a solid-liquid separation; or a solid product D which is obtained by directly drying to remove part or all of the solvent without the solid-liquid separation; or a solid product D which is obtained by the solid-liquid separation and drying to remove part or all of the solvent, wherein no re-crystallization step, such as removing the solvent for concentration or decreasing temperature and the like, is required, which makes the operation simple and easy, the cost low, and the production efficient. The mother liquid obtained by the solid-liquid separation can be repeatedly recycled to be used as the solvent C or a part thereof, for preparing the new solid product D, thereby further reducing the cost.

The endpoint of the reaction comprises achieving one of the following conditions:

I. The equilibrium pH of the system is 7-10, preferably a pH of 8-9;

II. the reactants of the designed amounts are exhausted; and

III. the amount of the solvent contained in the material D reaches the preset value, for example between 8%-25%.

The order of adding the reactants is not limited, but it is preferred that the material B is first mixed with a solvent C, and then the material A is added therein. Or, powder of the material A is sufficiently uniformly mixed with powder of the material B, and then they are gradually added into the solvent C and stirred thoroughly. The solid-liquid separation may be a common filtration or centrifugation, and it may also be other separation methods. The temperature of the reaction system was controlled between −20° C. to 60° C., preferably between 0° C.-25° C. A polymerization inhibitor may be added to reach a concentration of 0 mg/kg-1000 mg/kg, preferably 50-100 mg/kg. Oxygen or air can be fed from the bottom of the reaction system during the reaction, for the purpose of reducing the risk of polymerization.

The method for preparing solid acrylamido alkyl sulfonate of the present invention will be further described below in connection with specific examples.

EXAMPLE 1

90 g of water was added to a 1 L vessel and 36 g of solid NaOH was added, and they were stirred, dissolved and cooled; 0.03 g of polymerization inhibitor was added; and about 184 g of solid 2-acrylamido-2-methylpropanesulfonic acid was gradually added. The pH value of the reaction system was carefully detected in the later period of the reaction, and the addition of 2-acrylamido-2-methylpropanesulfonic acid was ended at pH of 8. During the reaction process, the temperature was maintained below 25° C., and the air is maintained as being fed from the bottom. The materials, which had undergone the reaction, were filtered, and the resulting solid was dried to obtain 2-acrylamido-2-methyl propanesulfonic acid salt solid product. The mother liquid obtained through filtration can be used to prepare the salt solution product of this substance, and can also be recycled for the preparation of the subsequent solid salt.

EXAMPLE 2

30 g of water was added to a 1 L vessel and 50 g of KOH powder was added, and they were uniformly stirred and cooled, without polymerization inhibitor added. 150 g of the mother liquid obtained through the filtration in the previous preparation process was slowly added, and solid 2-acrylamido-2-methylpropanesulfonic acid of a designed amount of 184 g was gradually added. During the process, the temperature was maintained between −20-10° C., and oxygen was maintained as being fed from the bottom. The materials, which had undergone the reaction, were filtered, and the solid obtained was dried to obtain 2-acrylamido-2-methyl propanesulfonic acid salt solid product.

EXAMPLE 3

180 g of mother liquid obtained in the previous separation process was added to a 1 L vessel and 52 g of Mg(OH)$_2$ was added, and they were uniformly stirred and cooled; 0.02 g of a polymerization inhibitor was added; and 368 g of solid 2-acrylamido-2-methylpropanesulfonic acid was gradually added and continuously uniformly mixed. The temperature was maintained between 30-50° C. during the process. A solid-liquid separation was performed, and the resulting solid material was dried to remove part of water so as to become a product.

EXAMPLE 4

2-acrylamido-2-methylpropanesulfonic acid powder was thoroughly uniformly mixed with CaO powder in a molar ratio (mole number) of 2:1 to obtain a mixed powder material; 100 g of water was added to a 1 L vessel and 0.2 g of a polymerization inhibitor was added; and the mixed powder material was gradually added therein with stirring until a theoretical calculated value of water content in the material reaches 15%. The temperature is maintained between 5~25° C. during the process, and the resulting wet solid material was directly used as a moisture-containing product without undergoing separation and drying.

EXAMPLE 5

2-acrylamido-2-methylpropanesulfonic acid powder was thoroughly uniformly mixed with NaOH powder in a molar ratio of 1:1 to obtain a mixed powder material; and 100 g of the mother liquid obtained through the filtration in the previous preparation process was added to a 1 L vessel and 150 g of the mixed powder material was gradually added therein and continuously uniformly mixed. The temperature is maintained between −5~15° C. during the process, and the resulting wet solid material was directly dried to remove all the water without undergoing the separation, so as to become a product.

EXAMPLE 6

100 g of 50% NaOH solution was added to a 1 L vessel, and 2-acrylamido-2-methylpropanesulfonic acid of a designed amount of 256 g was gradually added with sufficient stirring. The temperature was maintained between −10~10° C. during the process, and the materials which had undergone the reaction were dried at 100° C. under vacuum to obtain a solid product.

EXAMPLE 7

50 g of water and 100 g of mother liquid obtained by a solid-liquid separation in the previous preparation process were added to a 1 L vessel; 0.07 g of the polymerization inhibitor was added therein and the air was fed; and an equal-molar mixture of 2-acrylamido-2-methylpropanesulfonic acid and KOH powder was gradually added with sufficient stirring, the amount of the mixture being a designed amount of 600 g. The temperature was maintained between 10~20° C. during the process, and the materials which had undergone the reaction were dried and dehydrated to reach the preset moisture content, so as to be used as a product.

EXAMPLE 8

50% NaOH solution and 2-acrylamido-2-methylpropanesulfonic acid were uniformly continuously added to a continuous mixing apparatus which can continuously feed and continuously discharge material, with the two reactants in an equal molar ratio, and were thoroughly uniformly mixed in the case that the temperature was kept at 0~15° C. The material continuously discharged was dehydrated by an airflow drying device to obtain a product.

EXAMPLE 9

Mg(OH)$_2$ powder and 2-acrylamido-2-methylpropanesulfonic acid powder were thoroughly uniformly mixed in a molar ratio of 1:2, and this material mixture and water were uniformly continuously added into a continuous mixing apparatus which can continuously feed and continuously discharge material, in a weight ratio of 8.5:1.5, and the material continuously discharged was dehydrated by a drying device to obtain a product.

EXAMPLE 10

100 g of 25% ammonia water was added to a 1 L vessel, no polymerization inhibitor added and no air or oxygen fed; 2-acrylamido-2-methyl propanesulfonic acid was gradually added with stirring. The reaction was ended until pH value of the material falls within 8-9.5. The solid obtained through filtration was dried through air flow, to obtain a solid product.

EXAMPLE 11

45 g of methanol was added to a 1 L vessel, 25% aqueous ammonia was added, 22 g of solid LiOH was added, and they were uniformly stirred and cooled; 0.2 g of a polymerization inhibitor was added, and 2-acrylamido-2-methyl propanesulfonic acid was gradually added with stirring; and the reaction was ended when pH of the reaction material was measured as 10; and the resulting material was dried through air flow to obtain a solid product.

EXAMPLE 12

90 g of 50% trimethylamine was added to a 1 L vessel and 0.01 g of polymerization inhibitor was added; 2-acrylamido-2-methyl propanesulfonic acid was gradually added with stirring; the reaction was ended when pH of the reaction material was measured as 10, and a solid product was obtained by being dried at 50° C. under a negative pressure.

EXAMPLE 13

50 g of methanol was added to a 1 L vessel and 50 g of NaOH powder was added, and they were uniformly stirred and cooled; 50 g of dichloromethane was added; and 256 g of 2-acrylamido-2-methyl propane sulfonic acid powder was gradually added with stirring. The temperature was maintained at 0-10° C. during the reaction process. At the later period of the stirring, solvent and water produced in the reaction were removed by pumping a negative pressure while stirring the reaction material, until it was dried completely, to obtain a solid product.

EXAMPLE 14

50 g of ethanol was added to a 1 L vessel and 50 g of dichloroethane was added; and 200 g of a powder material mixture of 2-acrylamido-2-methylpropanesulfonic acid powder and KOH powder mixed in an equal molar was gradually added with stirring. The temperature was maintained at 0-10° C. during the process, and filtration was carried out; and the solid was dried at 50° C. under a negative pressure to obtain a solid product.

EXAMPLE 15

50 g of water was added to a 1 L vessel and 50 g of butylamine was added, and they were uniformly stirred and cooled; 30 g of acetone, 20 g of carbon tetrachloride, and 0.04 g of polymerization inhibitor were added therein; 2-acrylamido-2-methyl propanesulfonic acid power was gradually added with stirring until pH of 8-9.5. The temperature was maintained at 0-10° C. during the process and filtration was carried out. The solid was dried at 50° C. under a negative pressure to obtain a solid product.

EXAMPLE 16

150 g of water was added to a 1 L vessel, and 0.5 mol of KOH and 0.5 mol of CaO were added, and they were stirred, dissolved and cooled; 0.1 g of the polymerization inhibitor was added, and 1 mol of 2-acrylamido-2-methyl propanesulfonic acid was gradually added with stirring. During the process, the temperature was maintained below 40° C. and air is fed. Filtration was performed when the addition of materials was completed, and the solid was dried to obtain a product.

EXAMPLE 17

100 g of water was added to a 1 L vessel and 1 mol of LiOH was added, and they were stirred, dissolved and cooled; 0.08 g polymerization inhibitor was added therein; and about 1 mol of 2-acrylamidododecyl sulfonic acid was gradually added with stirring. The reaction was ended when the pH value of the reaction system was measured as 10 at the later period of the reaction. During the process, the temperature was maintained below 35° C., and the air was maintained as being fed from the bottom. The materials which had undergone the reaction were filtered, and the resulting solid was dried to obtain a 2-acrylamidododecyl sulfonic acid salt solid product.

EXAMPLE 18

50 g of methanol was added to a 1 L vessel, and 30 g of dichloromethane was added, and 0.01 g of polymerization inhibitor was added; and 300 g of a mixture of 2-acrylamido hexadecane sulphonic acid and NaOH powder mixed in an equal molar was gradually added with stirring. The temperature was maintained below 10° C. during the process. After the reaction of the materials added was completed, a 2-acrylamido hexadecane sulfonic acid salt solid product was obtained by being dried.

Preferred embodiments of the present invention were merely described above, and they are not intended to limit the scope of the invention. Without departing from the spirit of the design of the present invention, modifications and improvements of the technical solutions of the present invention made by the person skilled in the art shall fall within the scope of protection defined by the claims of the present invention.

INDUSTRIAL APPLICABILITY

The method for preparing solid acrylamido alkyl sulfonate of the present invention eliminates the costly and time-consuming steps in prior art, such as evaporation concentration or re-crystallization by decreasing temperature, which is employed in the process of obtaining a solid, thereby greatly improving the production efficiency of products, saving time, and reducing costs, which makes possible that industrialized production of such solid salts has economic value, thus it, as a new industrialized product, emerges on the market. The dry solid product prepared can be suitable for usages in non-aqueous systems, and can also be used in conditions where effective content of solution product needs to be more than 50~58%. In the method of the present invention, mother liquid obtained by the solid-liquid separation can be reused, which is environmentally-friendly and energy-saving, safe and reliable. The preparation method in the present invention is simple and feasible, and easy to operate, and has a great market prospect and a strong industrial applicability.

The invention claimed is:

1. A method for preparing solid acrylamido alkyl sulfonate, characterized by comprising steps of:
    (1) reacting a material A with a material B in a solvent C to generate a product D, the material A comprising at least one of compounds represented by the following general formula,

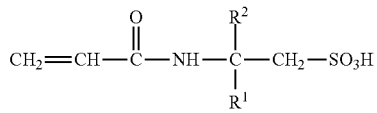

wherein $R^1$ and $R^2$ are hydrogen and/or an alkyl group containing from 1 to 20 carbon atoms, the material B is an alkaline substance, the product D is an acrylamido alkyl sulfonate, and the amount of the material A and material B is significantly in excess with respect to the solvent C, such that the amount of the product D generated by reaction between the material A and the material B exceeds a solubility of the product D under reaction condition, and the product D can be continuously generated and directly massively precipitated; and
    (2) collecting the solid product D, namely the product of the method.

2. The method for preparing solid acrylamido alkyl sulfonate according to claim 1, characterized in that the material A and material B are added in the way that: the material A and the material B are separately added into a solvent C, or during the addition of the materials, the material A and the material B, both in powder state, are sufficiently uniformly mixed in a proportion, and then added into the solvent C to react.

3. The method for preparing solid acrylamido alkyl sulfonate according to claim 1, characterized in that: feeding and discharging in Step (1) are performed in a batch-wise mode or a continuous mode or a combination of the two modes; and Step (2) is one of following conditions: direct collecting a moisture-containing solid product D containing a certain amount of solvent; direct drying without a solid-liquid separation to remove part of the solvent to obtain a solid product D; direct drying without a solid-liquid separation to remove all the solvent to obtain a solid product D; performing a solid-liquid separation and drying to remove part of the solvent to obtain a solid product D, and performing a solid-liquid separation and drying to remove all the solvent to obtain a solid product D.

4. The method for preparing solid acrylamido alkyl sulfonate according to claim 3, characterized in that liquid obtained by the solid-liquid separation is mother liquid, and the mother liquid obtained in the previous preparation is also included in the solvent C with content thereof being 0 to 100%.

5. The method for preparing solid acrylamido alkyl sulfonate according to claim 4, characterized in that the amount of the product D generated by reaction between the material A and the material B is greater than its solubility in the solvent C so that a significant amount of the product D is precipitated out, and a solid-liquid separation method is used to separate solid from liquid to obtain a solid and mother liquid.

6. The method for preparing solid acrylamido alkyl sulfonate according to claim 4, characterized in that the amount of the product D generated by reaction between the material A and the material B is much greater than its solubility in the solvent C, so that it is directly dried without a solid-liquid separation step.

7. The method for preparing solid acrylamido alkyl sulfonate according to claim 1, characterized in that:
    the preparation is performed at a temperature of −20° C.~60° C.;
    a mass ratio of the material A to the solvent C is in a range of 1:1~20:1;
    a molar ratio of the material A to the material B is in a range calculated in the following manner:
    for the material B showing monovalent in an acid-base reaction, the molar ratio of the material A to the material B is between 1:0.5 and 1:2; and
    for the material B showing bivalent in an acid-base reaction, the molar ratio of the material A to the material B is between 1:0.25 and 1:1, and
    in Step (1), the reaction has a reaction endpoint comprising one of the following conditions being reached:
        I. the equilibrium pH value of the system is between 5~11;
        II. the reactants of a designed amounts are exhausted; and
        III. the amount of the solvent contained in the product D reaches a preset value.

8. The method for preparing solid acrylamido alkyl sulfonate according to claim 7, characterized in that Step (1) further comprises adding a polymerization inhibitor of a concentration of 0 mg/kg~1000 mg/kg, and/or feeding oxygen or air.

9. The method for preparing solid acrylamido alkyl sulfonate according to claim 1, characterized in that the material B comprises at least one of the following substances: a metal oxide, a metal hydroxide, a compound having a structure of $NR_3R^4R^5$, wherein $R^3$ and $R^4$ and $R^5$ are hydrogen or an alkyl group, alkoxy group, and alkanol each containing 1 to 10 carbon atoms; and
    the solvent C comprises at least one of the following solvents: water, alcohol containing 1 to 8 carbon atoms, ketone containing 1 to 8 carbon atoms, ether containing 1 to 8 carbon atoms, ester containing 1 to 8 carbon atoms, and alkane and halogenated alkane containing 1 to 8 carbon atoms.

10. The method for preparing solid acrylamido alkyl sulfonate according to claim 9, characterized in the material B is one of NaOH, KOH, LiOH, $Ca(OH)_2$, $Mg(OH)_2$, $Na_2O$, $K_2O$, $Li_2O$, CaO, MgO, $NH_3$, methylamine, dimethylamine, trimethylamine, ethylamine, diethylamine, triethylamine, propylamine and butylamine, or a mixture of more of them.

\* \* \* \* \*